(12) United States Patent
Liu et al.

(10) Patent No.: US 9,054,640 B2
(45) Date of Patent: Jun. 9, 2015

(54) METHOD AND SYSTEM OF AN ULTRA HIGH Q SILICON CANTILEVER RESONATOR FOR THIN FILM INTERNAL FRICTION AND YOUNG'S MODULUS MEASUREMENTS

(71) Applicants: Xiao Liu, Fairfax, VA (US); Thomas H. Metcalf, Washington, DC (US)

(72) Inventors: Xiao Liu, Fairfax, VA (US); Thomas H. Metcalf, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 118 days.

(21) Appl. No.: 13/929,243

(22) Filed: Jun. 27, 2013

(65) Prior Publication Data

US 2014/0002203 A1    Jan. 2, 2014

Related U.S. Application Data

(60) Provisional application No. 61/665,048, filed on Jun. 27, 2012.

(51) Int. Cl.
*H03B 28/00* (2006.01)
*H01L 21/66* (2006.01)
*G01N 29/12* (2006.01)
*H03H 9/24* (2006.01)

(52) U.S. Cl.
CPC ............... *H03B 28/00* (2013.01); *H01L 22/12* (2013.01); *H01L 22/30* (2013.01); *H03H 9/2457* (2013.01); *G01N 2203/0282* (2013.01); *G01N 2203/0286* (2013.01); *G01N 29/12* (2013.01); *G01N 2291/02827* (2013.01); *G01N 2291/0427* (2013.01)

(58) Field of Classification Search
CPC ..................... H03B 2200/0018; H01L 41/053
USPC .................. 331/107 R, 116 R, 154, 156, 158; 310/320, 365–367
See application file for complete search history.

(56) References Cited

U.S. PATENT DOCUMENTS 6,817,255 B2 *    11/2004   Haque et al. ............. 73/862.638

OTHER PUBLICATIONS

Kiesewetter, L. et al.; Determination of Young's Moduli of micromechanical thin films using the resonance method; Sensors and Actuators; 1992; pp. 153-159; A, 35; Elsevier.

* cited by examiner

*Primary Examiner* — Joseph Chang
*Assistant Examiner* — Jeffrey Shin
(74) *Attorney, Agent, or Firm* — US Naval Research Laboratory; Suresh Koshy; John Leonard Young

(57) ABSTRACT

This invention provides an extremely accurate way to characterize the Young's modulus of thin film materials with thicknesses in the nanometer range. It takes advantage of a recently developed high Q silicon Young's modulus resonator (YMR), which has a record high quality factor of about fifty million in operation at temperatures below 10 degrees Kelvin (10K). Because of the high Q of the YMR, the temperature stability of the YMR's resonance frequency below 1K, and the extremely high degree of vibration isolation inherent in the inventive design, the relative resolution of the resonant frequency is typically in $2\times10^{-7}$. This is enough to resolve a resonant frequency shift after a deposition of a thin film onto the sensitive part of the resonator, and to compute the Young's modulus of thin film materials of even a few monolayers thickness.

20 Claims, 18 Drawing Sheets

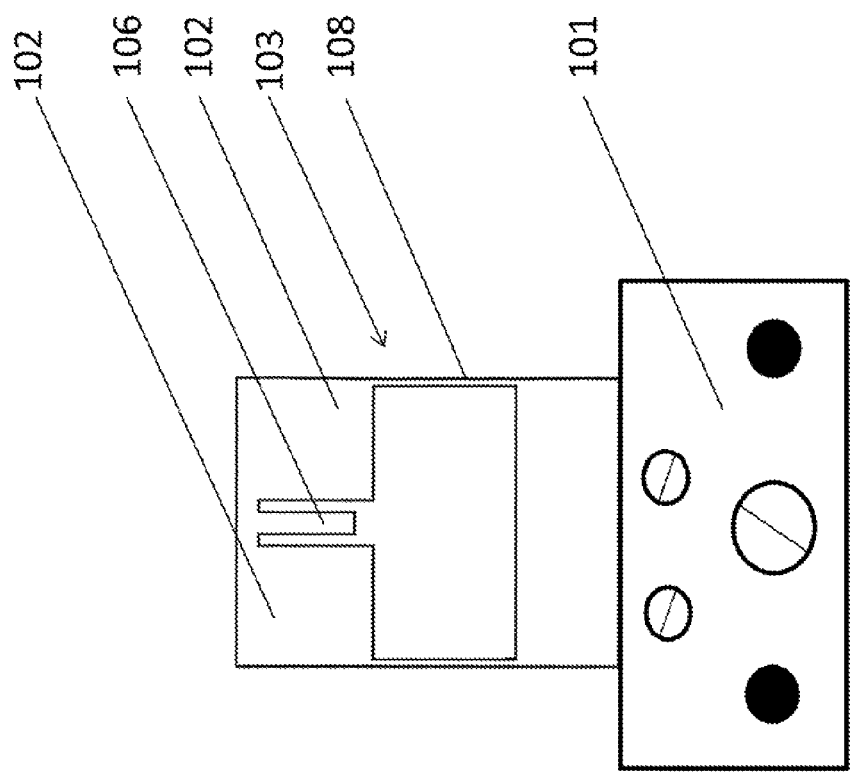

Finite Element Modeling for Design

Finite Element Modeling for Design $$Q^{-1}_{attachment} \propto \sqrt{\frac{\int_{foot}|w|^2}{\int_{resonator}|w|^2}}$$

METHOD AND SYSTEM OF AN ULTRA HIGH Q SILICON CANTILEVER RESONATOR FOR THIN FILM INTERNAL FRICTION AND YOUNG'S MODULUS MEASUREMENTS

RELATED APPLICATIONS

The instant U.S. patent application claims the benefit of domestic priority from and is related to U.S. Provisional Patent Application No. 61/665,048; METHOD AND SYSTEM OF AN ULTRA HIGH Q SILICON CANTILEVER RESONATOR FOR THIN FILM INTERNAL FRICTION AND YOUNG'S MODULUS MEASUREMENTS; filed on Jun. 27, 2012; whose inventors include Xiao Liu and Thomas H. Metcalf; where said U.S. Provisional Patent Application is herein incorporated by reference in its entirety.

FIELD OF THE INVENTION

The present invention relates to applications directed to manufacturing, packaging and deploying integrated circuit (IC) technology having increased speed, circuit density, as well as having small size and reliability in field operations, concerning various devices and platforms utilizing ICs. In particular, the instant invention is directed to the accurate and repeatable assessment of the reliability of thin film mechanical properties, such as measuring the elastic properties of thin film deposit configurations having thicknesses in the nano and sub-nanometer ranges. In order to make these measurements of thin film properties, the instant invention provides an accurate way to characterize the Young's modulus of thin film materials in such nano and sub-nanometer ranges, without destroying the deposited thin film configurations, during the measuring process, and measurements of Young's modulus achievable by the instant invention are at least one order of magnitude better than measurements achievable with existing measurement techniques.

BACKGROUND OF THE INVENTION

Thin film materials have been used in a wide variety of science and technology areas from computer chips and solar cells to wear-resistant coatings. However, it has been difficult to characterize the elastic properties of thin films with thicknesses in the nanometer range. In real-world applications, thin films are predominately attached to substrates. The mechanical properties of a composite thin film/substrate structure are typically dominated by the substrate due to its large thickness. According to Standard cantilever methods for characterization of elastic properties, resolution is lost, as the film thickness drops to the nano- and subnanometer range (see B. S. Berry et al., "Vibrating Reed Internal Friction Apparatus for Films and Foils", IBM Journal of Research and Development (1975) vol. 19, p. 334; and K. E. Petersen et al., "Young's modulus measurements of thin films using micromechanics, Journal of Applied Physics, (1979) vol. 50, p. 6761). (Further, according to J. J. Vlassak and W. D. Nix, Journal of Materials Research, "A new bulge test technique for the determination of Young's modulus and Poisson's ratio of thin films", (1992), vol. 7, p. 3242): "Releasing the thin films from substrates and measuring the elastic properties of free standing films has been the primary solution to this loss of resolution". In most circumstances, however, thin films are simply too fragile to withstand such experiments. In addition, there is no guarantee that the elastic properties would be the same for films on a substrate as for free standing films as the material properties of a thin film may often be sensitive to its interface.

There are two fundamental methods to measure the elastic moduli of a material: static and dynamic. In the static method, a local small stress is applied to the material and the corresponding strain is measured. Such measurements are typically inaccurate-often by a factor of 2 or more-because of contributions to the strain from material creep and local defects. More accurate modulus measurements are performed dynamically: by exciting the natural vibrations of a mechanical resonator made of the material in question (typically in the form of a beam) and by measuring its resonance frequencies. The accuracy of such measurements depends on the bandwidth of the resonator, which is directly related to the quality factor Q of the resonator as $\Delta f=f_0/Q$, where $f_0$ is the resonance frequency. The higher the Q is, the smaller the bandwidth will be, hence the higher the frequency resolution (lower $\Delta f$) of the resonator (see FIG. 8A and FIG. 8B, regarding variations of Q and frequency). According to L. Kiesewetter et al., "Determination of Young's moduli of micromechanical thin films using the resonance method" Sensors and Actuators A, 35 (1992) 153459, [by] using different excitation methods, including photothermal, acoustic and mechanical, the thin-beam resonating structures can be forced to vibrate. According D. F. McGuigan et al., "Measurements of the mechanical Q of single-crystal silicon at low temperatures", Low Temperature Physics, (1978) vol. 30, p. 621: Although there are specifically designed mechanical resonators with quality factors (Q) of $10^8$ to $10^9$, they are all bulky and not suitable or thin film modulus measurements. According to G. J. McShane, et al., "Young's modulus measurement of thin film materials using micro-cantilevers", Microengineering (2006) vol. 16, p. 1926: The thinnest cantilever-shaped resonators that are capable of carrying a thin film have a Q no larger than $10^6$. As a result, the elastic properties of many thin film materials are either poorly characterized or not characterized at all. According to Y.-H. Huh et al., "Measurement Mechanical Properties of Thin Film by Membrane Deflection Test" Experimental Mechanics, (2010) vol. 50, p. 429 and further according to Y. Cao, et al., "Nanoindentation measurements of the mechanical properties of polycrystalline Au and Ag thin films on silicon substrates: Effects of grain size and film thickness" Materials Science Engineering (2006) vol. A, pp. 427, 232: The measured values of Young's moduli of some commonly used materials can differ by a factor of two or more, depending on how the measurements were carried out.

The key to obtaining a high Q mechanical resonator is twofold. First, the resonator has to be made from an intrinsically low loss material, such as high-quality, single-crystal lightly doped silicon or un-doped silicon. Second, the resonance mode has to have excellent vibration isolation in order to minimize the external energy loss. Both methods have been successful. In particular, highly optimized vibration isolation is designed in and achieved by exemplary embodiments, as will be detailed below. Young's modulus measurements made with the exemplary Young's Modulus Resonator (YMR) embodiments described herein can be combined with shear modulus measurements from a double-paddle oscillator (DPO) to give a complete description of the elastic properties of isotropic thin film materials, including properties such as Poisson's ratio and bulk modulus, via known relations between the elastic constants.

FIG. 1A illustrates a picture of a Young's Modulus Resonator (YMR). FIG. 1B illustrates exemplary dimensions of the YMR in millimeters.

Further, according to R. Djakaria et al. Determination of Young's Modulus of Thin Films used in Embedded Passive Devices; 1997 Electronic Components and Technology Conference; IEEE; O-7803-3857-X/97; pp. 745-749 (1997): "The trends of increasing speed and circuit density in integrated circuits have created demands for new electronic packaging technologies. One technology that meets these demands uses multiple layers of thin film conductors, dielectrics and insulators to form embedded passive devices. One potential application of these embedded devices is the utilization of embedded thin film capacitors to replace surface mount technology (SMT) capacitors. For example, in portable communications devices there are typically more than 20 SMT capacitors . . . . The embedded design thus has a tremendous advantage over the SMT design due to the potential for a more compact package and for a more efficient manufacturing process. The thin films used for embedded passive devices are usually formed by evaporation, sputtering or electrolytical deposition. Under various conditions, these thin film assemblies deform or crack. Such phenomena, which adversely affect circuit performance, cannot be accurately predicted using the mechanical properties of bulk materials. Depending on how the thin film is formed, the mechanical properties are often different from those of the bulk material. To assess accurately the reliability of these thin films the mechanical properties, such as Young's modulus, need to be known . . . . There are several mechanical property measurement techniques which can be used to determine the Young's modulus of a thin film. Three commonly used . . . [measurement] techniques are microindentation, microbeam curvature and mechanical resonant frequency. In the microindenter technique, loads and penetrations of the indenter are continuously measured and recorded. An indentation curve of the load versus depth of penetration obtained from the test is used to determine the Young's modulus of the thin film being tested. One of the disadvantages of this technique is that the thin film being tested must be greater than about 20 micrometers in thickness. A relatively thick film is required so that the unloading microindentation curve enters the linear region as required to determine an elastic recovery value—one of the variables used to calculate the Young's modulus. The Vickers microindenter technique is commonly used for this measurement. In this technique a diamond pyramid indenter is used. The advantage of using the diamond indenter is that the technique can be used to test all materials due to diamond's hardness. A Vickers microindenter machine usually consists of three basic components: a diamond pyramid indenter, a load applying mechanism and an optical system to read the diagonal of the indentation. The diamond pyramid usually has a square base with an angle between its faces of 130-148 degrees. The optical system is usually similar to a regular optical microscope with a resolution of up to a micrometer . . . . In the microbeam curvature deflection technique, a microcantilever beam, with a thin film deposited onto one of its faces, is used to determine the Young's modulus of that thin film . . . [using] simple beam theory . . . by noting the deflection induced by a nano-indenter of a known load. The micro-cantilever beam is usually fabricated by a conventional silicon micromachining technique. The thin film is then deposited onto the prefabricated $SiO_2$ micro-cantilever beam by a sputtering process. Very high resolution equipment is needed to measure the very small dimensions associated with this technique. Typical thickness, width and length dimensions of the beams re 1.0, 20, and 30 micrometers . . . . In the mechanical resonant frequency technique, a micro-cantilever beam with a thin film deposited onto it, or with a stretched circular thin film membrane assembly, is vibrated electrostatically, and the Young's modulus of the thin film is determined from the mechanical resonant frequency of the assembly. A variable-frequency sinusoidal vibrator is applied to the tested assembly, and the movement of the tested assembly is detected by focusing a laser beam on the tested assembly and monitoring the reflected laser beam. The reflected beam is recorded as a function of frequency from which the mechanical resonant frequency can be determined. The mechanical resonant frequency technique is described by Peterson and Guarnieri . . . . The major disadvantages of this technique are the complexity associated with the fabrication of the tested specimen and the complexity of the testing apparatus . . . . The standard tensile test is one of the most common methods used to determine the mechanical properties of a material. The elastic deformation data obtained from this test are used to determine the Young's modulus of the tested material. In this test a specimen is extended under a steadily increasing load, and the external load is applied so that the specimen is in a state of uniaxial stress. Currently, the Young's modulus of the thin films used in the integrated circuits has not been determined by this technique due to the problem associated with separating the thin films from the silicon wafers without deforming them. To overcome this difficulty a flexible polyimide film is utilized as the substrate onto which the thin film is deposited. The polyimide and thin film assembly . . . [are] then used as the specimen of the standard tensile test. This technique . . . [allows] the determination of the thin film knowing the Young's modulus of the polyimide film. The thickness ratio of the thin film and the polyimide film of the tested polyimide-thin film specimen will determine the accuracy of this technique."

Conventional cantilever devices can measure the elastic properties of thin films (see (see B. S. Berry et al., "Vibrating Reed Internal Friction Apparatus for Films and Foils", IBM Journal of Research and Development (1975) vol. 19, p. 334; and K. E. Petersen et al., "Young's modulus measurements of thin films using micromechanics, Journal of Applied Physics, (1979) vol. 50, p. 6761); and G. J. McShane, et al. "Young's modulus measurement of thin film materials using micro-cantilevers". Microengineering (2006) vol. 16, p. 1926). Although efforts have been achieved which make very thin cantilevers (see K. E. Petersen et al., "Young's modulus measurements of thin films using micromechanics, Journal of Applied Physics, (1979) vol. 50, p. 6761); and G. J. McShane, et al. "Young's modulus measurement of thin film materials using micro-cantilevers", Microengineering (2006) vol. 16, p. 1926), the measurement resolution still suffers from the poor Q of those devices. Techniques have also been developed to remove the substrates in some circumstances and measure the Young's modulus of free standing films (see J. J. Vlassak and W. D. Nix, Journal of Materials Research, "A new bulge test technique for the determination of Young's modulus and Poisson's ratio of thin films", (1992), vol. 7, p. 3242). However, as mentioned above, the results may not apply to the film on substrate situation, which is far more common in real-world applications. The technique developed in this work is simple, robust, and reproducible. Most importantly, the finite element modeling design (see FIG. 6A and FIG. 6B) has greatly improved vibration isolation. In comparison to other techniques, exemplary embodiments of YMR exhibit a Q of at least ten times higher (i.e., at least one order of magnitude higher) than conventional techniques and frequency resolution at least one order of magnitude higher.

SUMMARY OF THE INVENTION

This application discloses an extremely accurate way to characterize the Young's modulus of thin film materials having thicknesses ranging from a few micrometers down to the subnanometer range. The instant invention discloses a high Q silicon Young's modulus resonator (YMR), which has a record high quality factor of about fifty million in operation at temperatures below 10 degrees Kelvin (10K). Because of the high Q of the YMR, the temperature stability of the YMR's resonance frequency below 1K, and the extremely high degree of vibration isolation inherent in the design of exemplary embodiments, the relative resolution of the achievable resonant frequency is typically that of about $2\times10^{-7}$. This is enough to resolve a resonant frequency shift after a deposition of a thin film onto the sensitive part of the resonator, and to compute the Young's modulus of thin film materials of even a few monolayers thickness. In exemplary embodiments, it is possible to determine the Young's modulus of one monolayer of atoms such as graphene.

According to G. J. McShane, et al. "Young's modulus measurement of thin film materials using micro-cantilevers", Microengineering (2006) vol. 16, p. 1926: The measurement sensitivity and resolution the YMR technique described in exemplary embodiments is at least one order of magnitude higher than that achieved with any other previous technique. According to X. Liu et al., "Low temperature elastic properties of chemically reduced and CVD-grown graphene thin films", Diamond Related Materials, (2010), vol. 19, p. 875: The instant invention is based on a double-paddle oscillator (DPO) technique, in which the shear modulus of subjects composed of a few monolayers of thin film material can be determined. Pairing this invention with the DPO technique will enable the complete elastic characterization of both Young's and shear moduli of thin films from a few micrometers down to subnanometer thickness.

BRIEF DESCRIPTION OF THE DRAWINGS

FIG. 1A illustrates a picture of a new cantilever resonator, based on a Young's Modulus Resonator (YMR) mounted in invar blocks 101.

FIG. 2A also illustrates a finite element calculation of grayscale relative displacement (out-of-plane displacement of a resonator).

DETAILED DESCRIPTION OF THE INVENTION

Figure 1B:
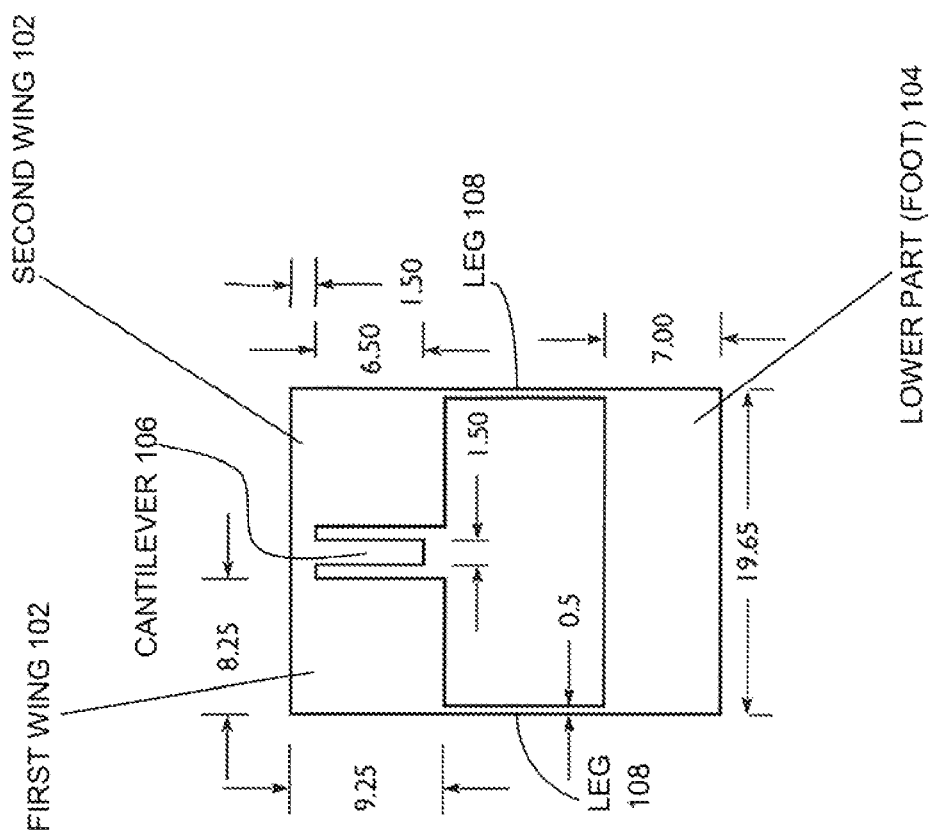
FIG. 1B illustrates the dimensions in millimeters of the YMR illustrated in FIG. 1A.

Preferred exemplary embodiments of the present invention are now described with reference to the figures, in which like reference numerals are generally used to indicate identical or functionally similar elements. While specific details of the preferred exemplary embodiments are discussed, it should be understood that this is done for illustrative purposes only. A person skilled in the relevant art will recognize that other configurations and arrangements can be used without departing from the spirit and scope of the preferred exemplary embodiments. It will also be apparent to a person skilled in the relevant art that this invention can also be employed in other applications. Further, the terms "a", "an", "first", "second" and "third" etc. used herein do not denote limitations of quantity, but rather denote the presence of one or more of the referenced items(s).

FIG. 1A illustrates an exemplary embodiment of the Young's Modulus Resonator (YMR) mounted in invar blocks 101 illustrated in FIG. 1A; and the dimensions (in millimeters) of the top surface of the YMR are shown FIG. 1B. YMRs are fabricated out of high purity silicon, lightly doped or un-doped, i.e., (crystallographic orientation/direction: <100> oriented), 0.3 mm thick silicon wafers, having resistivity greater than 5 k ohms-centimeters. The YMR can also be composed of one or more low loss, high Q semiconductor materials and/or compounds from group III-V and group IV semiconductor materials, including single crystal silicon, germanium, gallium arsenide, sapphire, quartz and diamond.

In the fabrication of exemplary embodiments, 300 micrometer thick undoped or lightly doped single crystal silicon wafers in <100> orientation are used as substrates. The vibration isolation principle used to achieve high Q would equally apply to silicon substrates of any thickness, crystallographic orientation and any doping levels of silicon wafers, as long as high Q characteristics can be maintained. Likewise, exemplary embodiments equally encompass any other substrates which can be characterized as high Q/low loss, such as single crystal sapphire, quartz, GaAs, diamonds etc. One of the key features of the exemplary embodiments is the vibration isolation achieved by FEM design principles incorporated herein, which reduce the external loss. In addition, for the same reason, any proportional scaling of the YMR will retain the vibration isolation characteristics of the various exemplary embodiments. In an exemplary embodiment using 100 micron thick silicon wafer and reducing the overall dimension by a factor of three during photolithographic patterning would increase the resonance frequency by a factor of three and retain the same high Q characteristic of the resonator. This has been proven to be true using the DPO technique. Therefore, this invention operates inclusive of all the above variations in substrate materials and proportional scaling of the geometry.

Figure 1C:
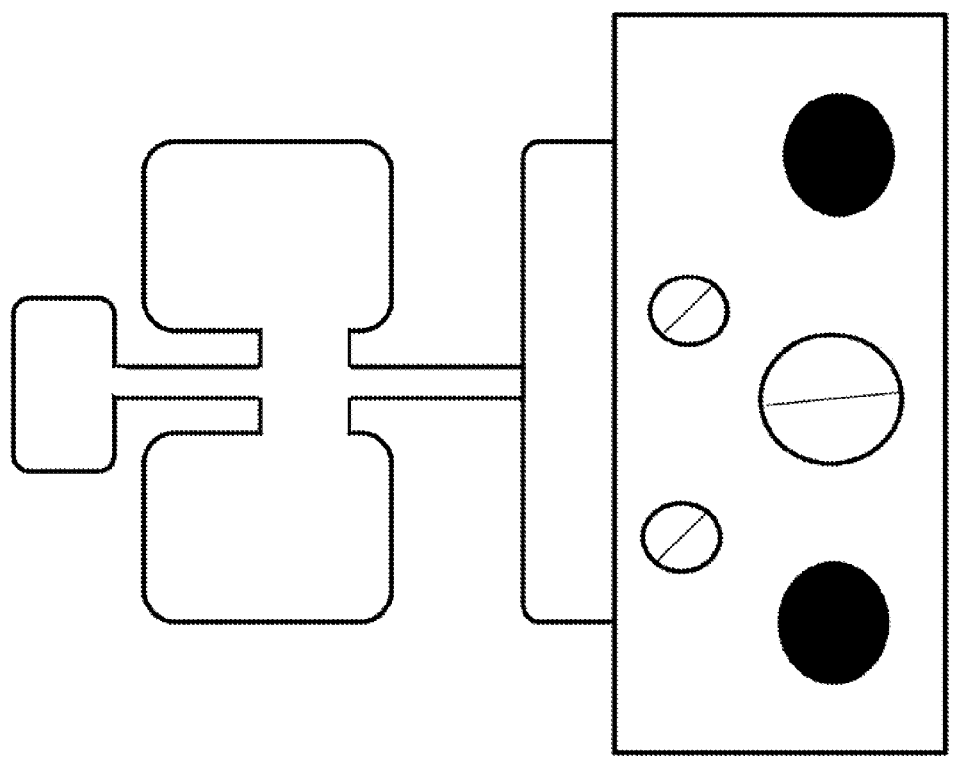
FIG. 1C illustrates a torsional resonator.
Figure 1D:
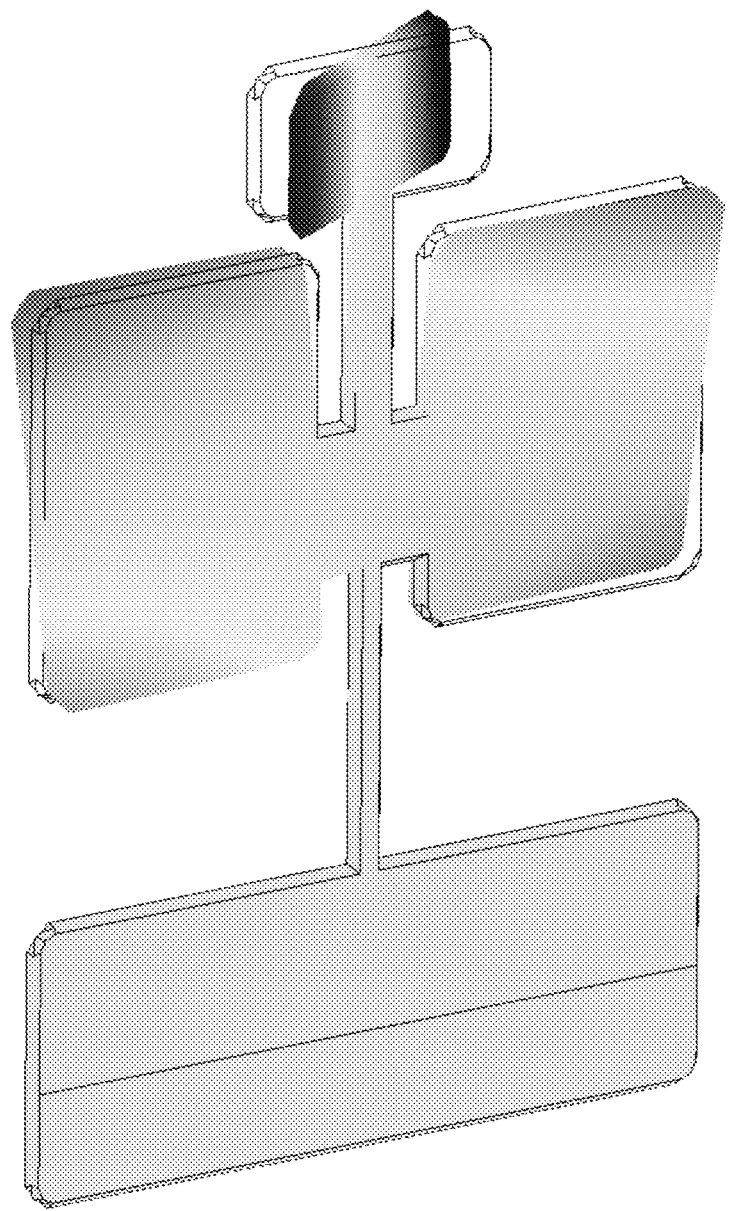
FIG. 1D illustrates out-of-plane displacement of the torsional resonator, illustrated in FIG. 1C.

The fabrication process involves photolithography, reactive ion etching, wet Chemical etching, and electron beam evaporation, and which can be the same processes as those used for the DPO. The overall dimension of a YMR is 28 mm high, 20 mm wide, and 0.3 mm thick. The dimensions in FIG. 1 are those used in the photolithographic process and patterned on the top surface of the silicon wafer. This pattern is rendered in a silicon nitride layer, which serves as a mask for the wet chemical etch step. The wet chemical etching exposes crystallographic orientation: <111> faces as sidewalls, which protrude outward at 35.3 degrees from the vertical. Thus, the corresponding features on the bottom are 0.212 nm further outward from those on the top.

Referring to FIG. 1A and FIG. 1B, the YMR consists of upper part 103 and lower part 104, connected by two thin legs 108. The lower part 104, also called the foot, is clamped to a block using invar screws and a precision torque wrench (see FIG. 1A). As invar matches silicon in thermal expansion from 300K to below 1K, this mounting method minimizes the effect of thermal contraction during cool down and ensures reproducibility after repeated remounting of the same YMR. The upper part 103 consists of a small cantilever 106 in the center, and two wings 102 on each side. The main axes of the YMR are along the crystallographic direction: <110> orientation. On the back of the YMR, a metal film (30 Angstroms Cr and 500 Angstroms Au) is deposited from the lower part 104 up to the wings 102, but not on the cantilever 106. Two electrodes are coupled to the wings 102 from the back side, for electrostatic actuation and detection. Exemplary embodiments include an antisymmetric cantilever (ASC), oscillating at approximately 8600 Hz; which is the 7th fundamental resonance mode of the YMR, where, such design has an exceptionally high Q which equals approximately $5 \times 10^7$ at low temperatures (T less than 10 K) and in cryogenic vacuum, (i.e., less than $10^{-3}$ Torr), which is reproducible within ±10% for different YMRs.

Figure 2A:
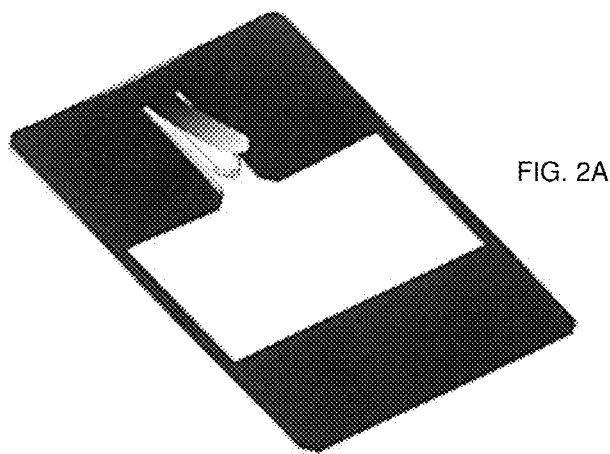
FIG. 2A illustrates a finite element calculation of displacement in the high-Q mode, which is the $7^{th}$ resonant mode; grayscale represents relative displacement (out-of-plane displacement of the new cantilever resonator).
Figure 2B:
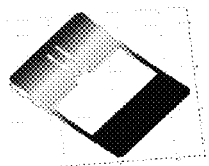
FIG. 2B through FIG. 2G represent the first 6 resonant modes.
Figure 2C:
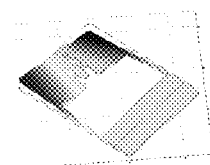
Figure 2D:
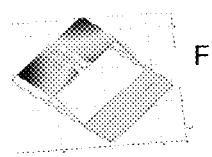
Figure 2E:
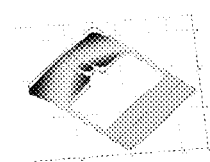
Figure 2F:
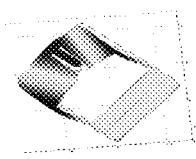
Figure 2G:
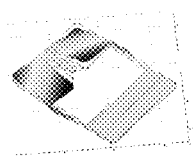
Figure 2H:
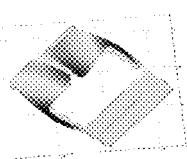
FIG. 2H represents the $8^{th}$ resonant mode.
Figure 3A:
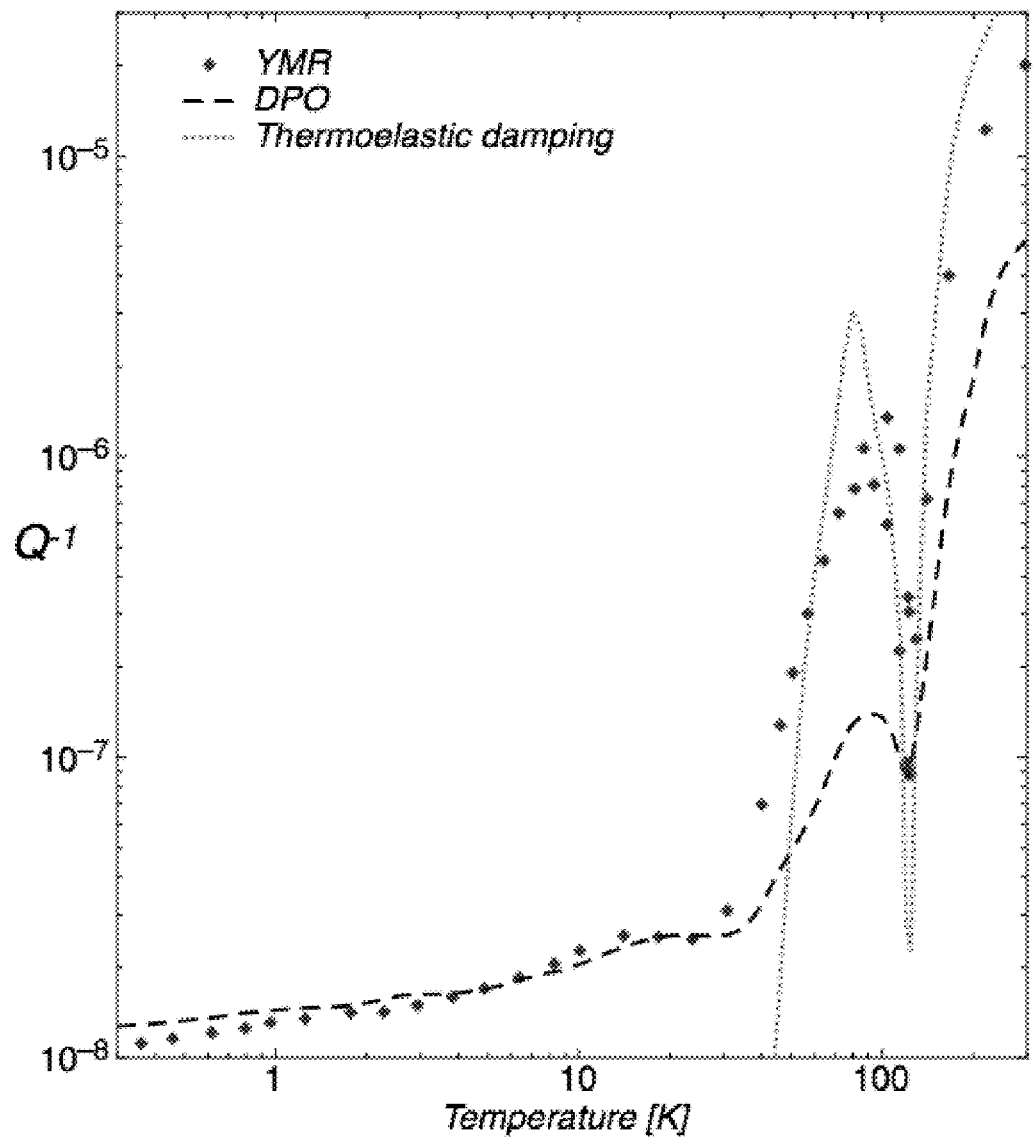
FIG. 3A illustrates a graphic of the measured 1/Q versus temperature for a YMR (diamond symbol), shown together with typical values for the double-paddle-oscillator (DPO) (dashed line) and Zener's thermoelastic (damping) loss (dotted line).
Figure 3B:
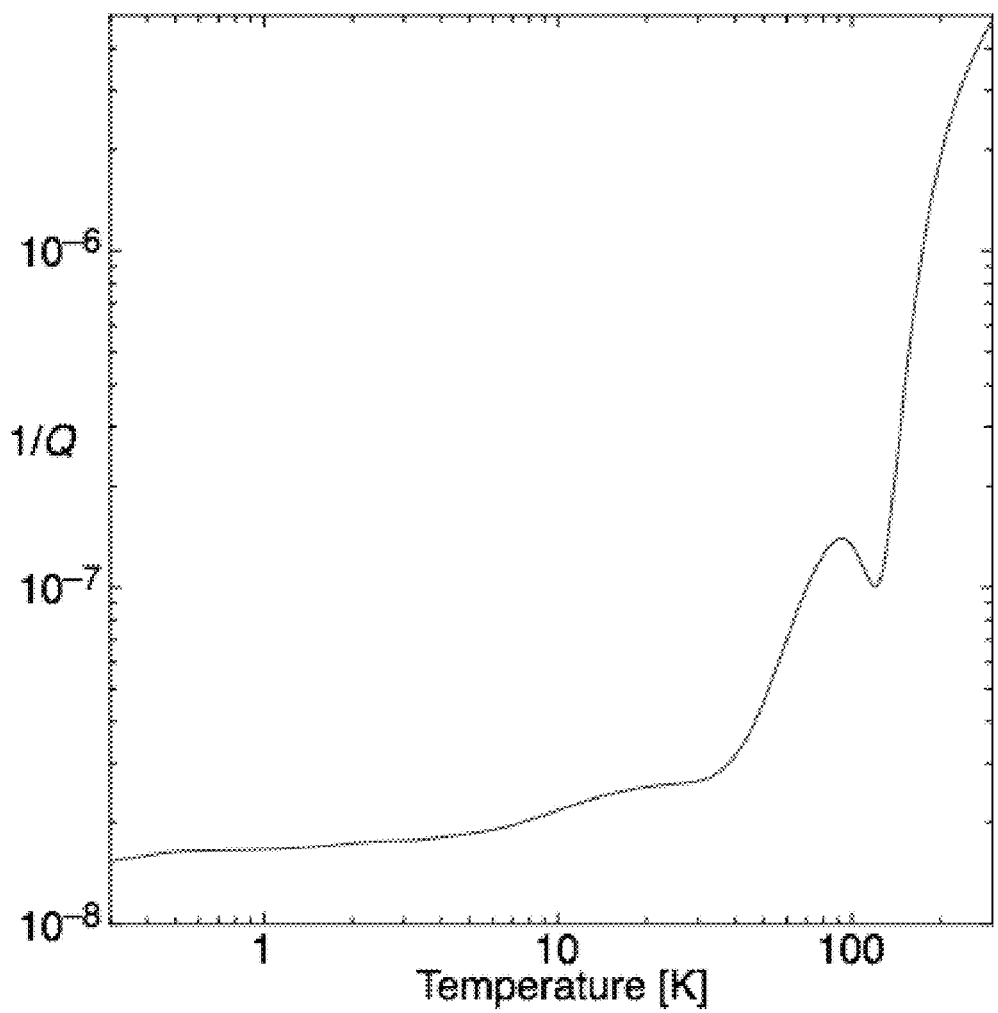
FIG. 3B illustrates a graphic of just the measured 1/Q versus temperature of a torsional resonator.

The high Q is attributed to the YMR's unique design and mode shape. During oscillation in the ASC mode, the cantilever 106 and the wings vibrate predominantly out-of-plane and 180 degrees out-of phase, so that most of the vibration is contained in the upper part 103 of the resonator. The legs 108 and the lower part 104 of the resonator exhibit minimal vibration, thus minimizing the external loss; see the finite-element (FEM) calculation of the displacement in the vibration mode illustrated in FIG. 2; the FEM calculations optimize resonator dimensions (also, see FIG. 6A and FIG. 6B, finite element modeling for design). The internal friction $Q^{-1}$ (the inverse of Q) of the ASC mode as a function of temperature is shown in FIG. 3A, together with the $Q^{-1}$ of the DPO for comparison. Above 30K, the $Q^{-1}$ is dominated (in both resonators) by thermoelastic loss (i.e., thermoelastic damping), a phenomenon in which thermal currents induced by flexural motion are in resonance with mechanical vibrations, (see C. Zener, "Internal Friction in Solids. I. Theory of internal Friction in Reeds", Physical Review, (1937), vol. 52, pp. 230-235, the computed the thermoelastic loss (due to damping) is in good agreement with the results, also shown in FIG. The "dip" near 120 K corresponds to the region where the thermal expansion coefficient of silicon passes through zero. The $Q^{-1}$ versus T behavior of the YMR above 30 K mimics that of the DPO, but is larger by a factor of 7, as the YMR motion is nearly entirely flexural and only) a small amount of the DPO motion is flexural (see B. H. Houston et al., "Thermoelastic loss in microscale oscillators", Applied Physics Letters, (2002) vol. 80, pp. 1300-1302). FIG. 2A illustrates a finite element calculation of displacement in high-Q mode; grayscale represents relative displacement.

The YMR discussed in exemplary embodiments (see FIG. 1A and FIG. 2A) is similar to the DPO technique, in that the YMR has the same fabrication process, has almost the same overall dimensions, can use the same holder, has the same measurement electronics, has a comparable low temperature Q, has operating characteristics at 8400 Hz; has large wings on long thin supports and the wings vibrate out-of-phase with the element.

Fabrication of the YMR includes 300 micrometer silicon wafers; coated with low pressure chemical vapor deposition (LPCVD) Silicon Nitride (SiN); with crystal cleavage (cleave) along the <110> crystal plane direction; photolithography, plasma etch patterns SiN; hot potassium hydroxide (KOH) etching microfabrication releases structures; and SiN removed with hydrofluoric acid.

Except that the DPO characteristics include: neck twists (see FIG. 1D), 5500 Hz operating characteristics, and sample films deposited on neck.

Figures 6A, 6B:
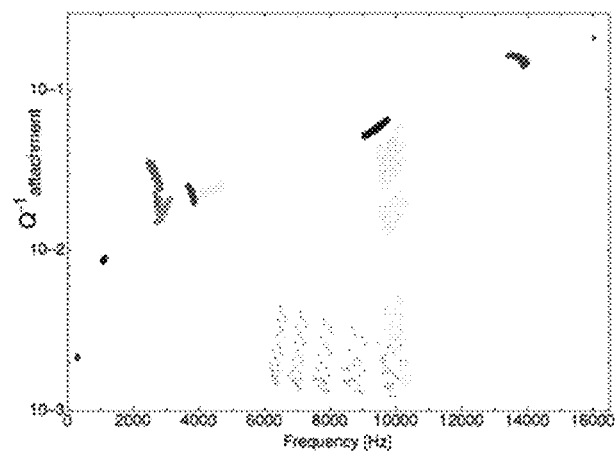
FIG. 6A illustrates a FEM calculation algorithm in terms of foot (lower part 104) attachment.
FIG. 6B illustrates attachment loss and resonant frequency for the first 10 resonance modes for a set of 144 candidate resonator dimensions. Different symbols denote the different resonance modes. Attachment loss is calculated using the formula shown in FIG. 6A. The plus symbols, clustered in the middle bottom of the figure, represent the high-Q, antisymmetric cantilever (ASC) mode. Frequencies and attachment losses of other modes tend to cluster, giving substantial overlap. For calculation of candidate dimensions, cantilever 106 length varied between 5.5 mm and 7.5 mm in 5 increments, wing 102 width varied between 7.5 mm and 8.25 mm in 4 increments, and wing 102 length varied between 8.5 mm and 9.8 mm in 6 increments.

The precise values of the dimensions of the YMR were determined with two objectives in mind: first, to maximize the vibration isolation, and second, to provide compatibility with the DPO sample holder and experimental apparatus. The DPO compatibility requirement fixed the overall width and height of the YMR. To maximize vibration isolation, FEM calculations are performed on an exhaustive set of candidate dimensions. Referring to FIG. 6A and FIG. 6B, FEM is used to explore possible dimension space to minimize attachment loss via the foot of a resonator. FIG. 6B illustrates attachment loss and resonant frequency for the first 10 resonance modes for a set of 144 candidate resonator dimensions. Different symbols denote the different resonance modes. Attachment loss is calculated using the formula shown in FIG. 6A. The plus symbols, clustered in the middle bottom of the figure, represent the high-Q, antisymmetric cantilever (ASC) mode. Frequencies and attachment losses of other modes tend to cluster, giving substantial overlap. For calculation of candidate dimensions, cantilever 106 length varied between 5.5 mm and 7.5 mm in 5 increments, wing 102 width varied between 7.5 mm and 8.25 mm in 4 increments, and wing 102 length varied between 8.5 mm and 9.8 mm in 6 increments. Thus, FEM can be used to explore possible dimension space to avoid close mode crossings. In addition, FEM can be used to explore possible dimension space to ensure electrical pickup. (See FIG. 7 and FIG. 1B).

Figure 7:
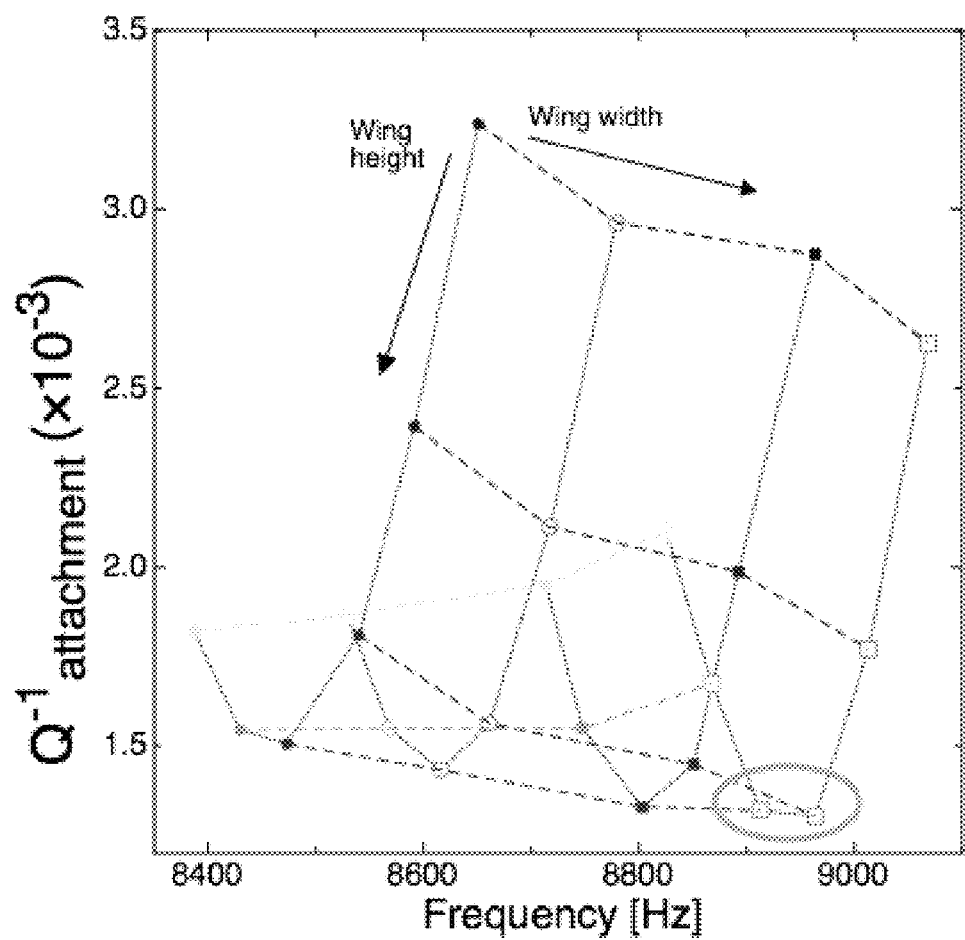
FIG. 7 illustrates a close-up graphic representing attachment loss/frequency pairs disclosed above in FIG. 6B (showing only antisymmetric cantilever (ASC) mode frequencies for a cantilever 106 which is 6 mm long. Each symbol shows the attachment loss and ASC mode resonant frequency for one set of candidate dimensions. The two circled data points in the lower right corner of the graph represent the best performing candidate dimensions according to the criteria used, and were the basis of the dimensions used for the device and shown in FIG. 1B.
Figure 8A:
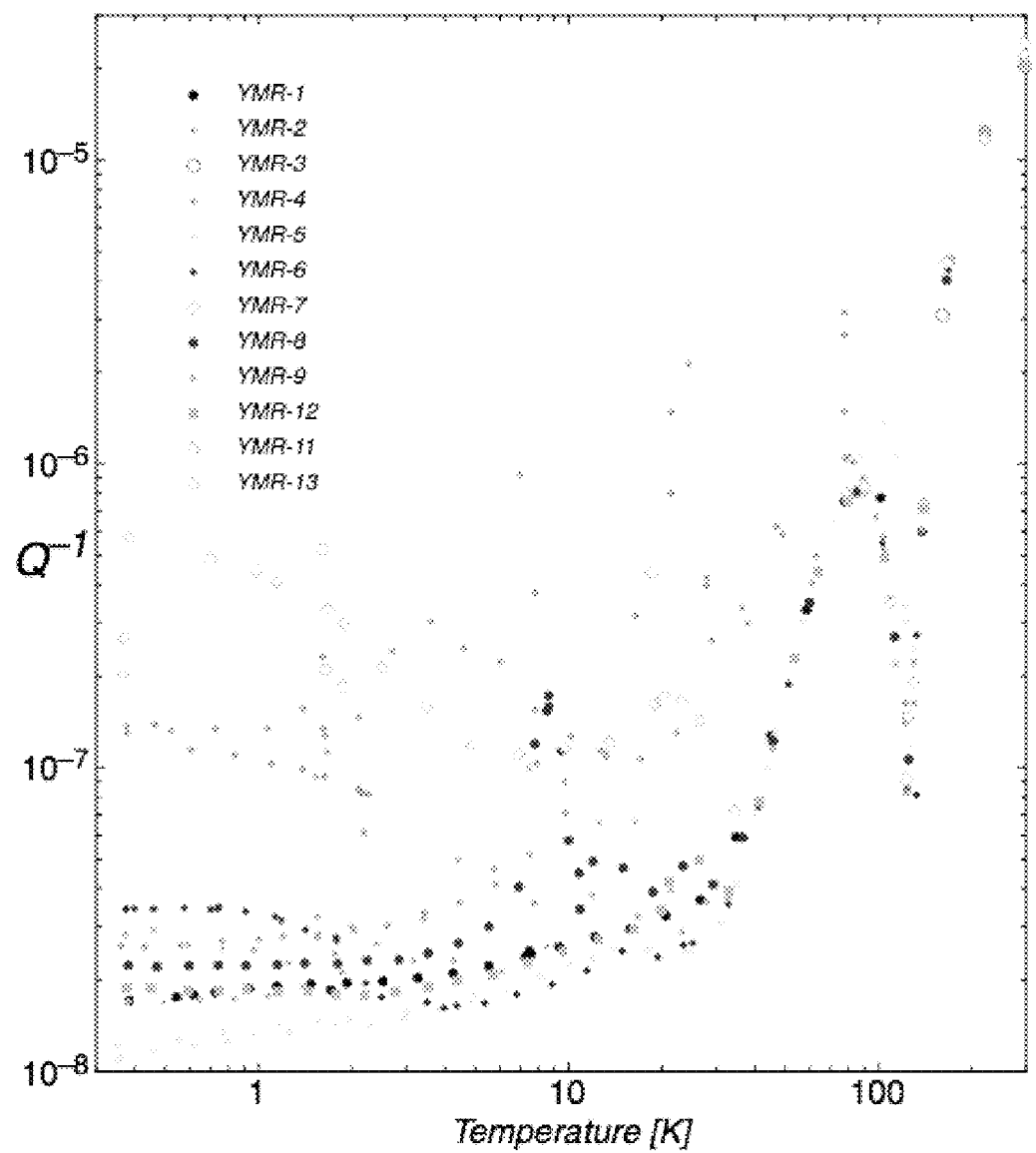
FIG. 8A illustrates the 1/Q versus temperature of the ASC resonance mode for the first twelve YMR samples that were fabricated and measured. These data illustrate the production yield and sample-sample reproducibility of ASC mode Q.
Figure 8B:
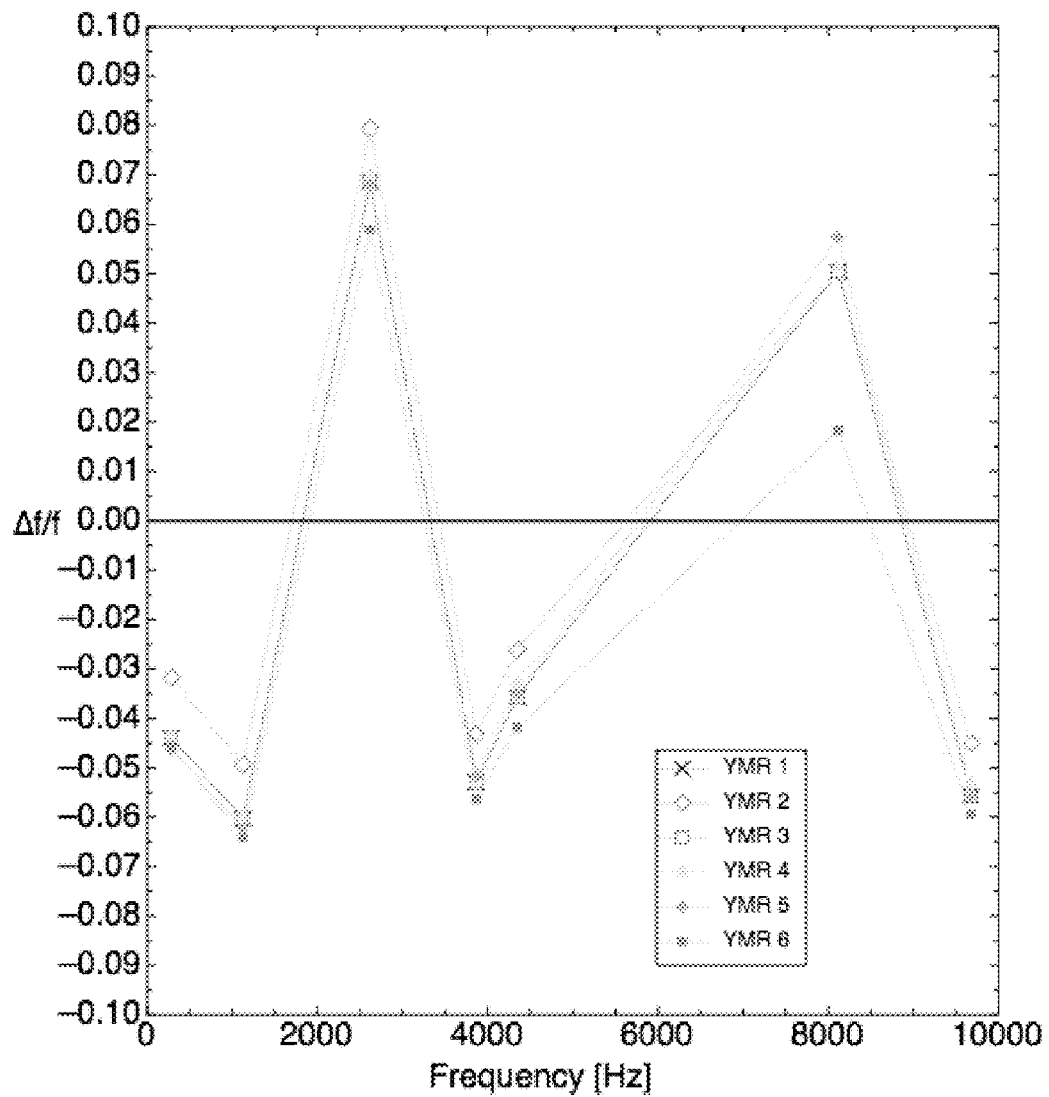
FIG. 8B illustrates the relative difference in frequency between the FEM calculations of resonance frequency and the first 6 YMR samples that were fabricated and measured. Seven of the first eight resonance modes are shown; the $4^{th}$ resonance mode cannot be measured with the existing experimental instruments. Different symbols represent different YMR samples and each data point represents one resonant frequency of one sample. The data presented in FIG. 8B illustrates the reproducibility of resonant frequency of the various resonant modes.

Referring to FIG. 7 and FIG. 1B, FIG. 7 illustrates a close-up graphic representing attachment loss/frequency pairs disclosed above in FIG. 6B (showing only antisymmetric cantilever (ASC) mode frequencies for a cantilever 106 which is 6 mm long. Each symbol shows the attachment loss and ASC mode resonant frequency for one set of candidate dimensions. The dashed lines connect candidate dimensions of equal wing 102 widths, while the dotted lines connect candidate dimensions of equal wing 102 lengths. The range of candidate wing 102 lengths is between 8.5 mm and 9.75 mm in 0.25 mm increments, the range of candidate wing 102 widths is between 7.5 mm and 8.25 mm in 0.25 mm increments. The two circled data points in the lower right corner of the graph represent the best performing candidate dimensions according to the criteria used, and were the basis of the dimensions used for the device and shown in FIG. 1B. These calculations give a displacement profile for each resonant mode, from which the relative distribution of vibrational energy can be calculated. The final design uses the set of dimensions which minimizes the fraction of ASC-mode vibrational energy in the foot of the resonator (see X. Liu et al., "On the modes and loss mechanisms of a high Q mechanical oscillator", Applied Physics Letters, (2001) vol. 78, pp. 1346-1348). FIG. 3A illustrates a graphic of the measured $Q^{-1}$ (i.e., 1/Q) versus temperature for a YMR, shown together with a typical value for the DPO (dashed line) and Zener's thermoelastic loss (dotted line).

Deposition of a thin film onto the upper part 103 of a YMR changes its resonance frequency, $f_{osc}$, as well as its internal friction, $1/Q_{osc}$ from those of a bare YMR, $f_{sub}$ and $1/Q_{sub}$, respectively. From the differences, the Young's modulus and the internal friction of the film can be calculated through the following:

$$\frac{f_{osc} - f_{sub}}{f_{sub}} = \frac{\alpha t_{film}}{2 t_{sub}} \left[ \frac{3 Y_{film}}{Y_{sub}} - \frac{\rho_{film}}{\rho_{sub}} \right], \quad (1)$$

$$Q_{film}^{-1} = \frac{Y_{sub} t_{sub}}{3 Y_{film} \alpha t_{film}} (Q_{osc}^{-1} - Q_{sub}^{-1}) + Q_{osc}^{-1}, \quad (2)$$

where t, ρ, and Y are thicknesses, mass densities, and Young's moduli of substrate and film, respectively; and where α is the film coverage factor. The Young's modulus of silicon along the cantilever 106 of the YMR (crystallographic orientation: <110> direction) is $Y_{sub}$=171 GPa, and $t_{sub}$=300 micrometers.

Figure 4:
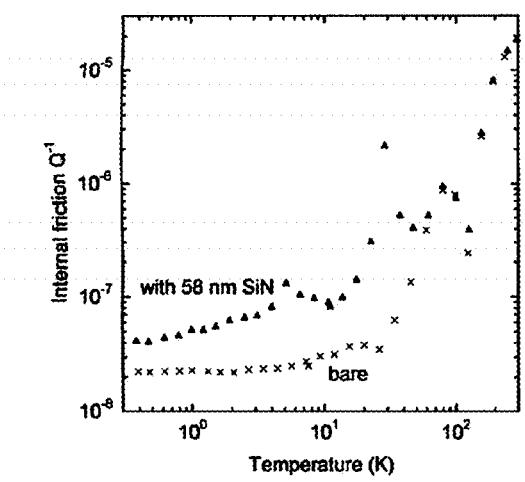
FIG. 4 illustrates internal friction of a bare YMR and the same YMR carrying a 58 nm thick low pressure chemical vapor deposition (LPCVD) SiN film.
Figure 5:
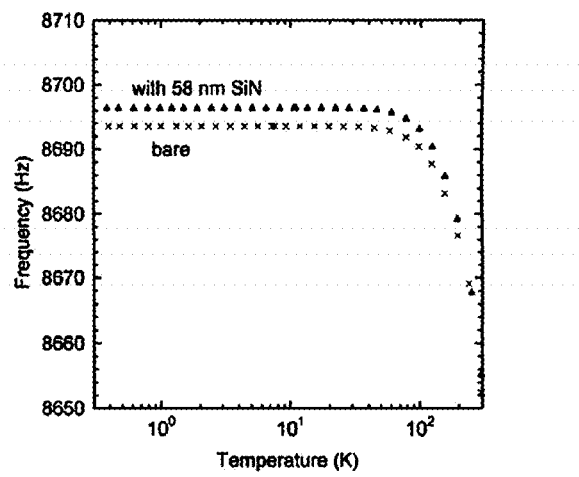
FIG. 5 illustrates the resonance frequency of a bare YMR and the same YMR carrying a 58 nanometer thick LPCVD SiN film.
Figure 9A:
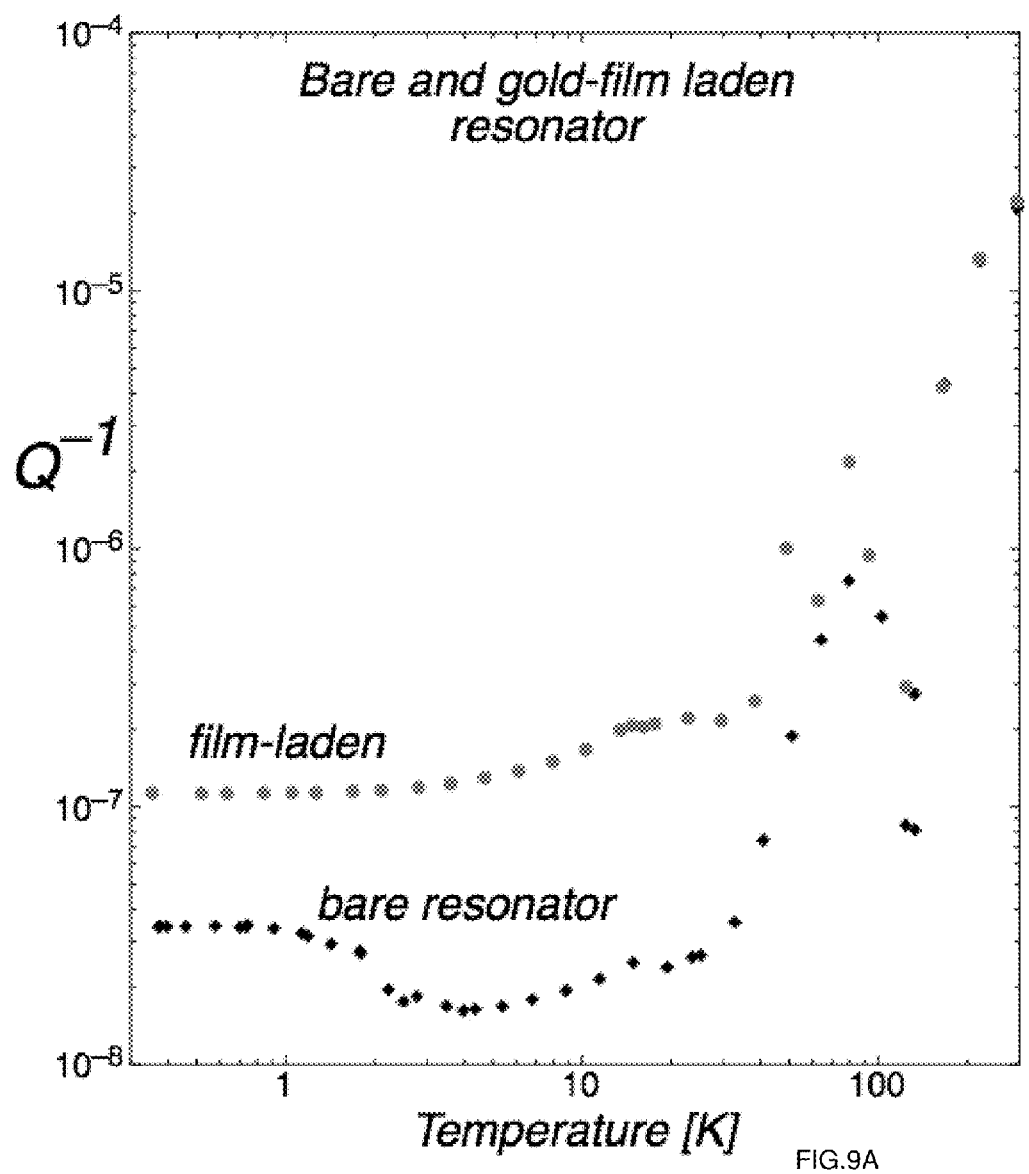
FIG. 9A illustrates a graphic of 1/Q measurements involving gold films in terms of 1/Q versus Temperature (K).
Figure 9B:
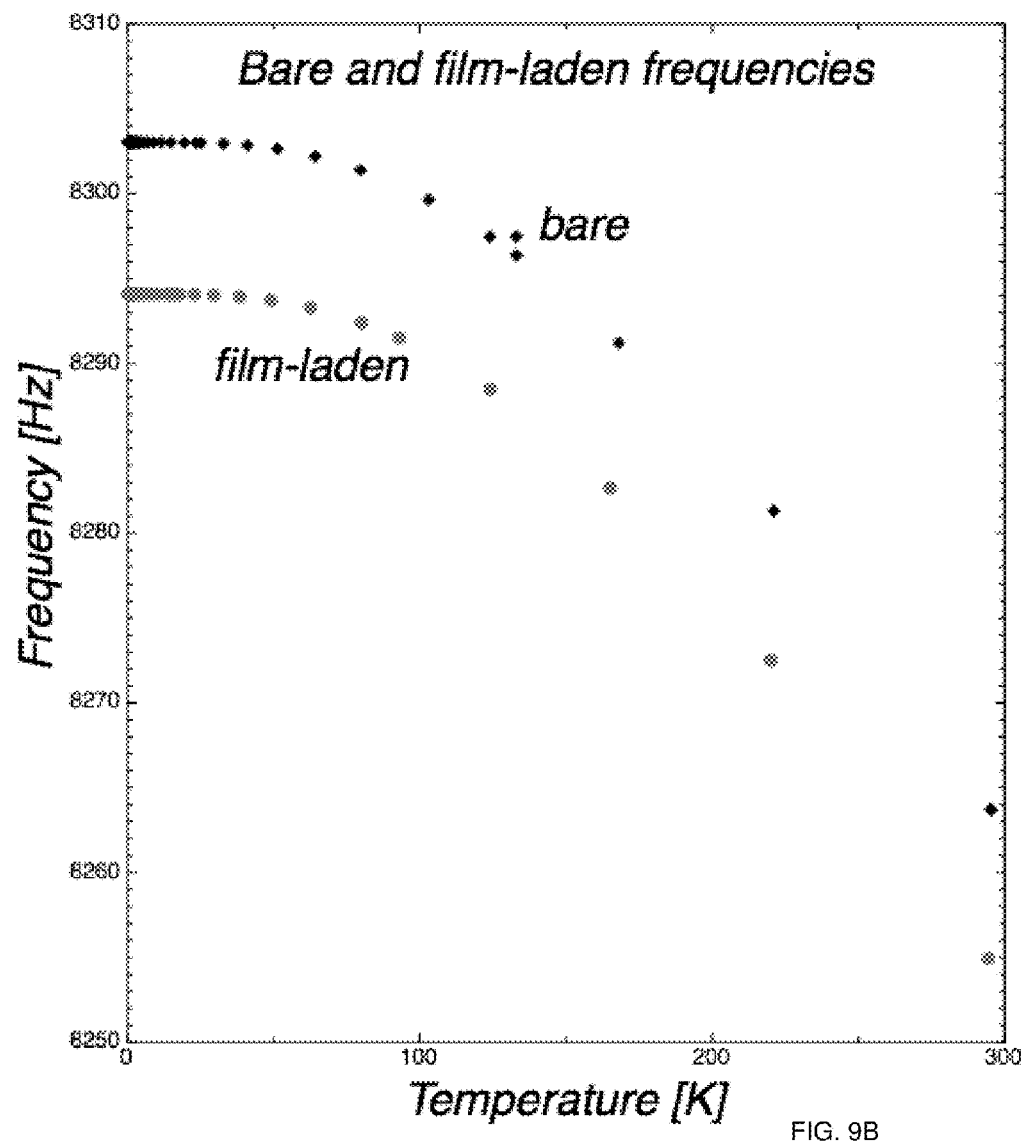
FIG. 9B illustrates a graphic of Young's Modulus measurements involving gold films in terms of Frequency in Hz versus Temperature in degrees Kelvin.
Figure 10A:
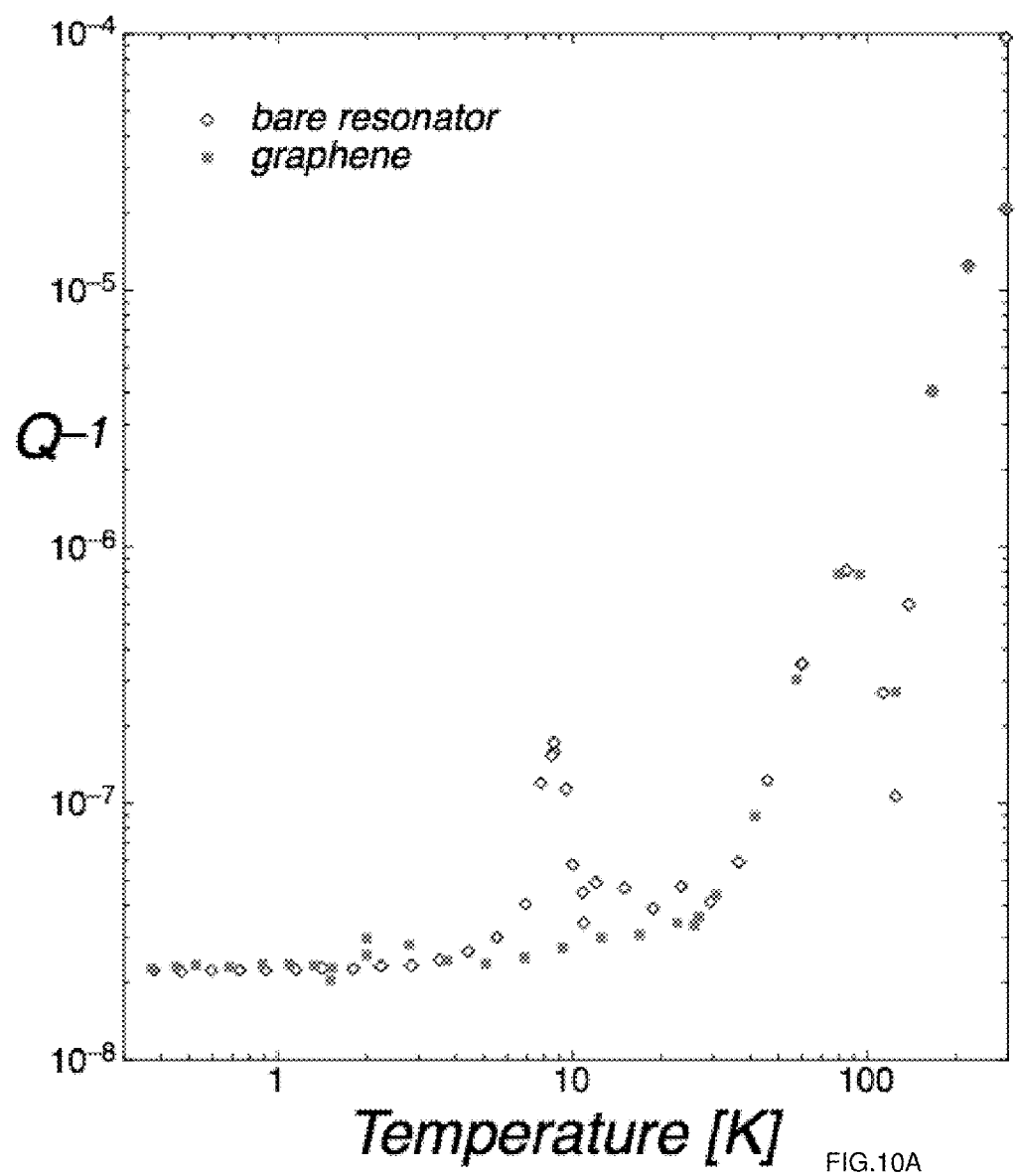
FIG. 10A illustrates a graphic of $Q^{-1}$ measurements involving graphene in terms of $Q^{-1}$ versus Temperature (K).
Figure 10B:
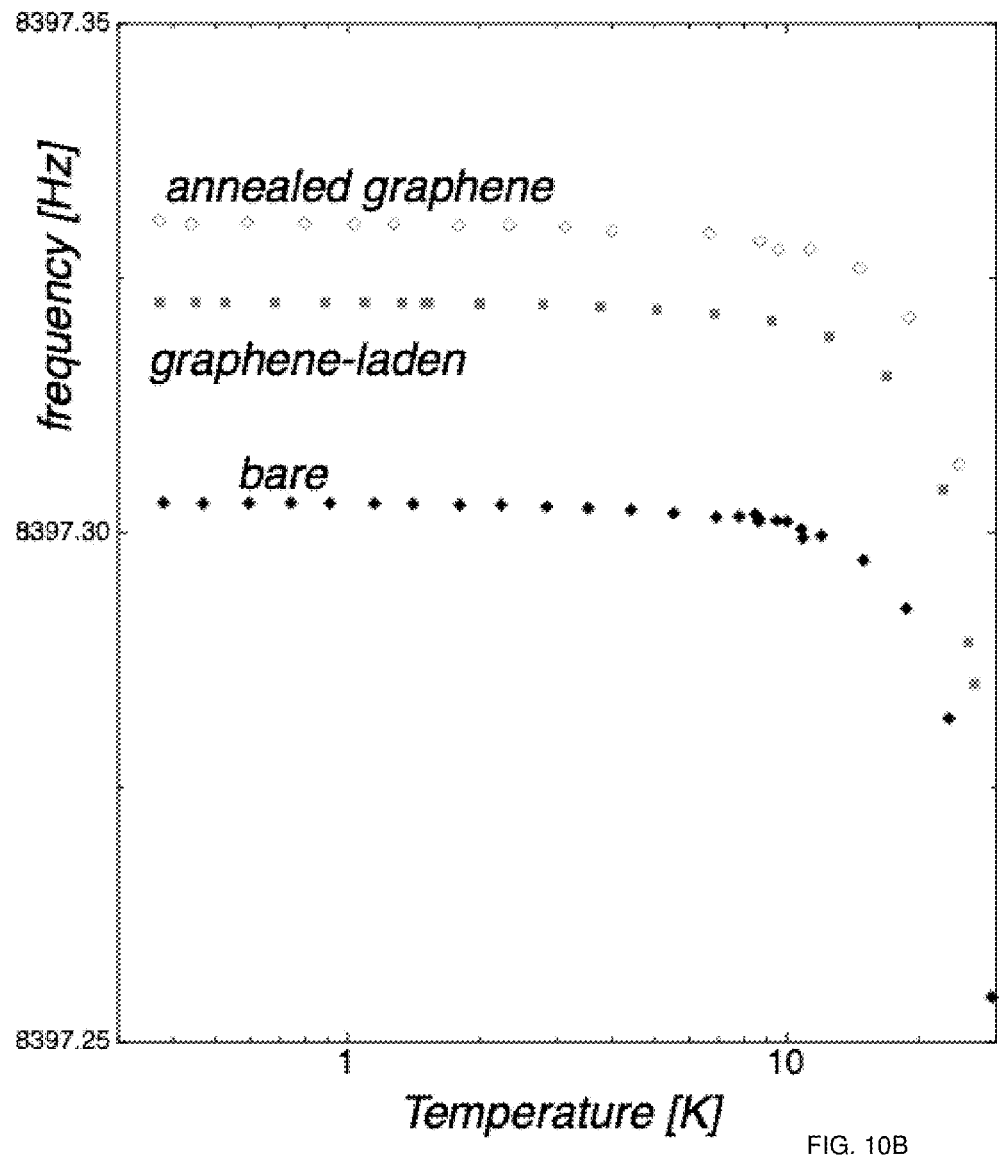
FIG. 10B illustrates a graphic of Young's Modulus measurements involving graphene in terms of Frequency in Hz versus Temperature in degrees Kelvin.
Figure 11A:
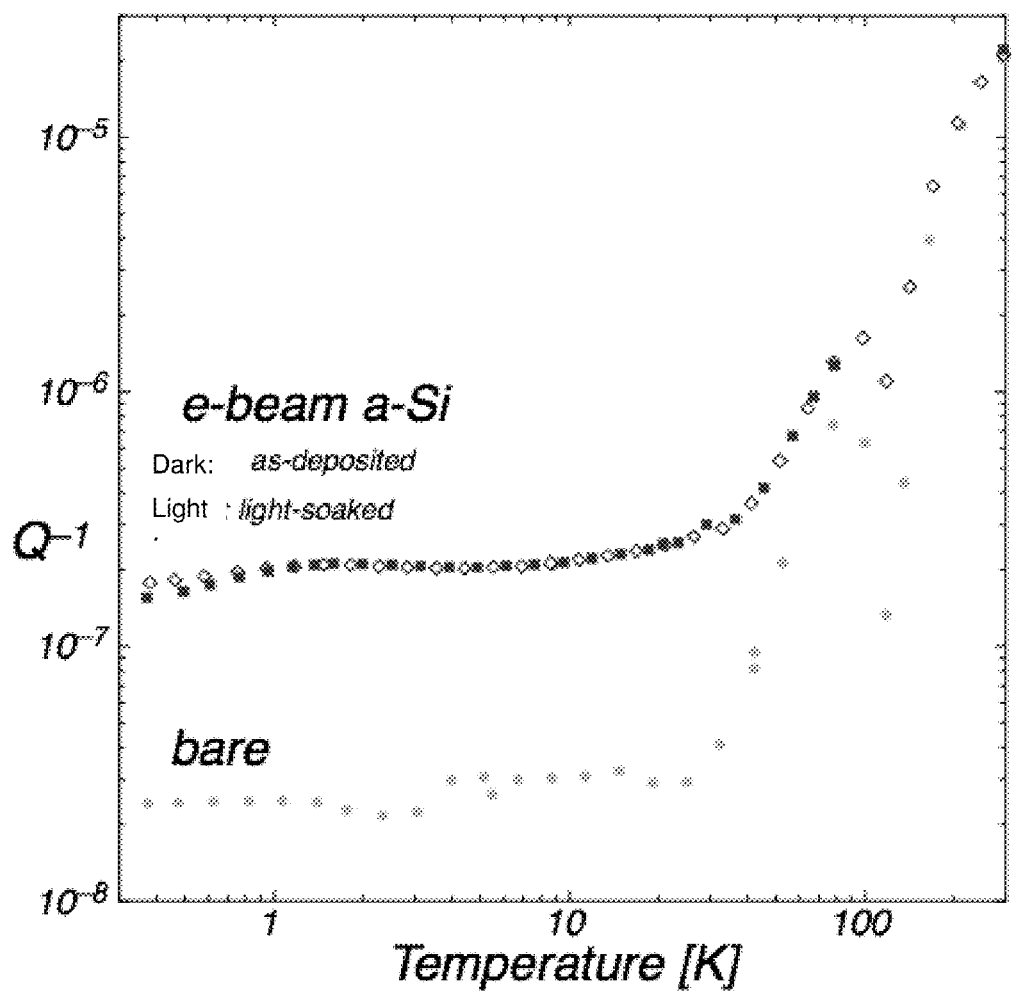
FIG. 11A illustrates a graphic of $Q^{-1}$ measurements involving e-beam amorphous Silicon in terms of $Q^{-1}$ versus Temperature (K).
Figure 11B:
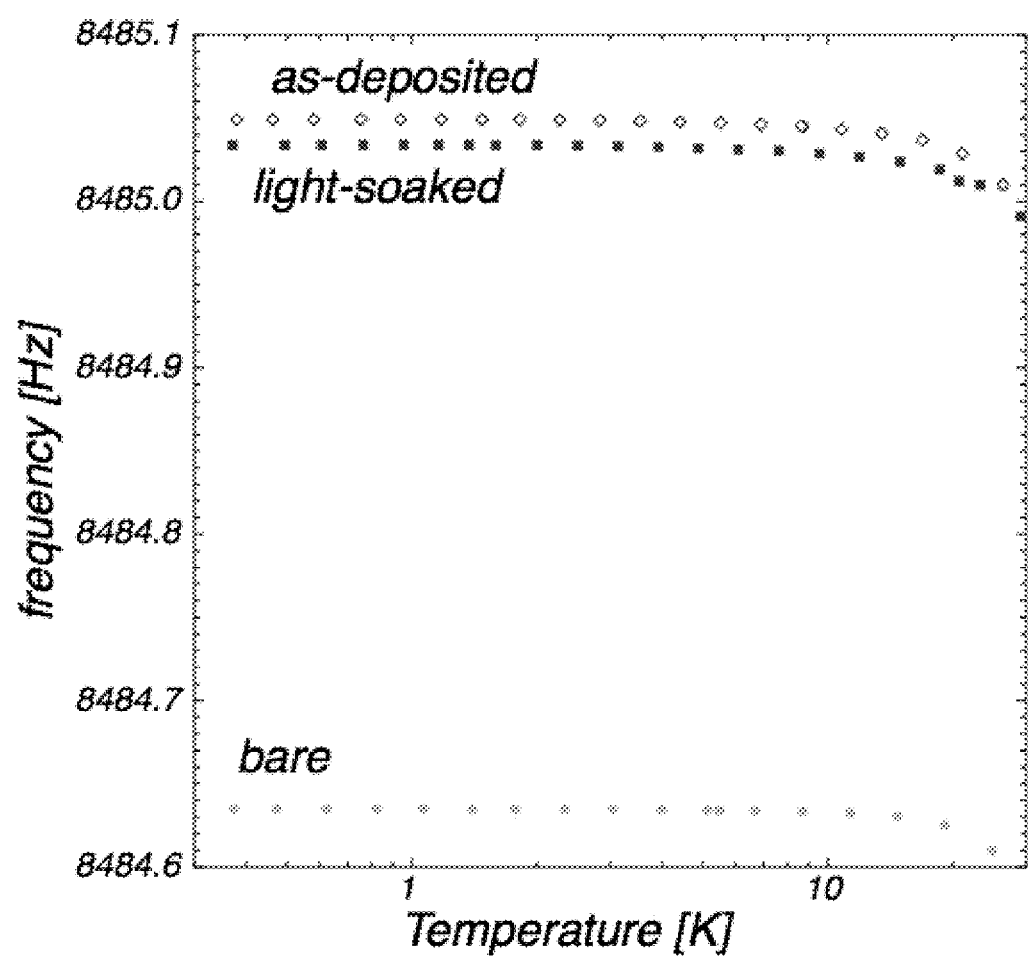
FIG. 11B illustrates a graphic of Young's Modulus measurements involving e-beam amorphous Silicon in terms of Frequency in Hz versus Temperature in degrees Kelvin, as a function of light soaking.

Preliminary Q and Young's modulus measurements have been conducted on a variety of substances, including gold (see FIG. 9A and FIG. 9B), amorphous silicon (see FIG. 11A and FIG. 11B, where light soaking does not change Q but does change Y, regarding the e-beam measurement of amorphous silicon), amorphous silicon nitride (see FIG. 4 and FIG. 5), and monolayer graphene (see FIG. 10A and FIG. 10B, regarding measurement of graphene: annealed graphene; graphene-laden; and bare resonators). FIG. 4 illustrates $Q^{-1}$ measurements and FIG. 5 illustrates resonance frequency measurements of a YMR both before and after being coated with a layer of a low-pressure chemical-vapor deposited silicon nitride film with thickness of 58 nm. Using equations (1) and (2) above and mass density (ρ=2.68 g/cm³ measured separately by the Rutherford Backscattering method), $Y_{film}$=270 GPa was obtained, and also, $1/Q_{film}$=2~6×10⁻⁵ was obtained at below 10K.

The key to the resonator design of the exemplary embodiments is the vibration isolation achieved from the combination of the long, thin legs 108 that attach the wings to the lower part 104 of the resonator; and the anti-symmetric vibration of the cantilever 106 vis-a-vis the wings 102, which contain the vibrational energy in the upper part 103 of the resonator to minimize loss via the attachment. This vibration isolation leads to a quality factor that's an order of magnitude higher than that of previous cantilever designs for thin film measurements, with a corresponding improvement in the sensitivity and repeatability of the measurements. The YMR has been designed as a complement to the DPO, in both a scientific and a technical sense. Scientifically, the Young's modulus and shear modulus measurements from the two resonators give a complete picture of the elastic constants of an isotropic thin film material. Technically, the YMR can be held in the same mounting block as the DPO and can be measured with the same electronic apparatus as the DPO, thus eliminating the need for modifications to the experimental measurement setup when changing resonators.

While the exemplary embodiments have been particularly shown and described with reference to preferred embodiments thereof, it will be understood by those skilled in the art that the preferred embodiments including any first, second and/or third exemplary embodiments have been presented by way of example only, and not limitation; furthermore, various changes in form and details can be made therein without departing from the spirit and scope of the invention. Thus, the breadth and scope of the present exemplary embodiments should not be limited by any one or more of the above described preferred exemplary embodiment(s), but should be defined only in accordance with the following claims and their equivalents. All references cited herein, including issued U.S. patents, or any other references, are each entirely incorporated by reference herein, including all data, tables, figures, and text presented in the cited references. Also, it is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The foregoing description of the specific embodiments will so fully reveal the general nature of the invention that others can, by applying knowledge and skill within the art, readily modify and/or adapt for various applications such specific embodiments, without undue experimentation, and without departing from the general concept of the present invention. Therefore, such adaptations and modifications are intended to be within the meaning and range of equivalents of the disclosed embodiments claimed herein and below, based on the teaching and guidance presented herein and the claims that follow:

What is claimed is:

1. A method, of assessing reliability of thin film mechanical properties of materials having thin film deposit configurations, wherein a cantilever resonator composed of a low loss high Q semiconductor substrate wafer, includes an upper part consisting of a cantilever formed in a center of the upper part of the semiconductor substrate wafer and a first wing and a second wing formed on each side of the cantilever, wherein the semiconductor substrate wafer further includes a lower part, wherein the lower part of the semiconductor substrate wafer is connected to the upper part of the semiconductor substrate wafer by a first leg and a second leg, wherein the second part of the semiconductor substrate wafer is clamped to a metallic block having a low coefficient of thermal expansion, and wherein a first electrode connected to the first wing and a second electrode connected to the second wing communicatively coupling an electrostatic actuation device and an electrostatic detection device to the cantilever resonator; the method comprising:
determining a measure of stiffness of an elastic material composing an at least one thin film deposition material of a plurality of thin film deposition materials deposited on the cantilever resonator, by:
exciting a plurality of vibrations of the cantilever resonator, using one or more of a plurality of excitation methods, including electronic, electrostatic, acoustic, photothermal and mechanical excitation methods; and
detecting, reading and recording, using a computer electro-optical device, measurements from a variation in a mechanical resonant frequency, wherein a thickness of the at least one thin film deposition material ranges from a subnanometer thickness measured value to a micrometer thickness measured value, and wherein, after assessing the measure of stiffness of the elastic material, the at least one thin film deposition material ranging from the subnanometer thickness measured value to the micrometer thickness measured value is free of structural deformation and free of structural deconstruction.

2. The method according to claim 1, wherein the semiconductor substrate wafer has a crystallographic orientation of <100>.

3. The method according to claim 1, wherein a plurality of main axes of the semiconductor substrate wafer exist along the crystallographic direction: <110> orientation.

4. The method according to claim 1, wherein mechanical excitation includes an antisymmetric cantilever (ASC) device oscillating at approximately 8600 Hz.

5. The method according to claim 1, further including isolating vibration to the upper part of the cantilever resonator.

6. The method according to claim 1, wherein the first and second wings vibrate 180 degrees out-of-phase, and wherein the cantilever resonator has a resolution of achievable resonant frequency of about $2 \times 10^{-7}$, at about 10 degrees Kelvin.

7. The method according to claim 1, wherein the low loss high Q semiconductor substrate wafer is composed of a material selected from a group of materials consisting of group III-V and group IV semiconductors.

8. The method according to claim 7, wherein the low loss high Q semiconductor substrate wafer includes an at least one or more of single crystal silicon, germanium, gallium arsenide, sapphire, quartz and diamond, wherein the at least one or more of single crystal silicon, germanium, gallium arsenide, sapphire, quartz and diamond is one of undoped and lightly doped.

9. The method according to claim 8, wherein the low loss high Q semiconductor substrate wafer is 300 micrometers thick.

10. A cantilever resonator apparatus, having thin film deposition configurations, measuring reliability of thin film mechanical properties, the apparatus comprising:
a semiconductor substrate wafer, having low loss and high Q properties, further having a crystallographic orientation of <100>, wherein the semiconductor substrate wafer includes an upper part consisting of a cantilever formed in a center of the upper part of the semiconductor substrate wafer and a first wing and a second wing formed on each side of the cantilever, wherein the semiconductor substrate wafer further includes a lower part, wherein the lower part of the semiconductor substrate wafer is connected to the upper part of the semiconductor substrate wafer by a first leg and a second leg, and wherein the second part of the semiconductor substrate wafer is clamped to a metallic block having a low coefficient of thermal expansion; and
a first electrode connected to the first wing and a second electrode connected to the second wing communicatively coupling an electrostatic actuation device and an electrostatic detection device to the cantilever resonator apparatus.

11. The cantilever resonator apparatus according to claim 10, wherein a plurality of main axes of the semiconductor substrate wafer exist along the crystallographic direction: <110> orientation.

12. The cantilever resonator apparatus according to claim 10, wherein the electrostatic actuation device includes an antisymmetric cantilever (ASC) device oscillating at approximately 8600 Hz.

13. The cantilever resonator apparatus according to claim 10, wherein, the low loss high Q semiconductor substrate wafer is composed of a material selected from a group of materials consisting of group III-V and group IV semiconductors, including an at least one or more of single crystal silicon, germanium, gallium arsenide, sapphire, quartz and diamond, and wherein the cantilever resonator apparatus operating characteristics and thicknesses are scalable using a semiconductor substrate wafer having a thickness in a range from about 100 microns thick to about at least 300 microns thick.

14. The cantilever resonator apparatus according to claim 10, wherein the lower part of the cantilever resonator apparatus is free of vibration, because the first and second legs isolate vibration to the upper part of the cantilever resonator apparatus, which includes the first and second wings and the cantilever formed in the center of the upper part, and wherein the first and second wings and the cantilever formed in the center of the upper part contain vibrational energy.

15. The cantilever resonator apparatus according to claim 10, wherein the first and second wings vibrate 180 degrees out-of-phase in relation with the cantilever, and wherein the cantilever resonator apparatus further exhibits a resolution of achievable resonant frequency of about $2 \times 10^{-7}$, at about 10 degrees Kelvin.

16. A Young's Modulus Resonator (YMR), wherein the YMR comprising:
a silicon substrate wafer composed of a single crystal silicon having silicon characteristics selected from a group of silicon characteristics consisting of lightly doped silicon and un-doped silicon, and having dimensions of 28 mm high, 20 mm wide and 0.3 mm thick;

the YMR pattern is rendered in a silicon nitride layer mask for a wet chemical etch process exposing crystallographic orientation: <111> faces as sidewalls protruding outward at 35.3 degrees from vertical, wherein corresponding bottom features are 0.212 mm further outward from top features;

the silicon substrate wafer further comprising an upper part consisting of a cantilever formed in a center of the upper part of the silicon substrate wafer and a first wing and a second wing formed on each side of the cantilever, wherein the silicon wafer further includes a lower part, wherein the lower part of the silicon substrate wafer is connected to the upper part and isolated from the upper part by two thin legs of the cantilever formed in the center of the upper part connecting wings to a base of the YMR, and wherein the first and second wings and the cantilever formed in the center of the upper part contain vibrational energy;

at least one of a plurality of thin film material selected from a group of thin film material consisting of gold (Au), graphene, various forms of silicon and silicon compounds, including silicon nitrides, and including silicon mono-nitride (SiN) are deposited onto the silicon substrate wafer in a range of thicknesses selected from a group of thickness consisting of monolayers-nanometer and a few micrometers by a plurality of deposition operations selected from a group of operations consisting of one or more of evaporation, sputtering, electrolytical deposition, and low pressure chemical vapor deposition operations; wherein Finite Element Measurement calculations calculate dimensions of the YMR, to obtain high Q and vibration isolation, and wherein the lower part is clamp mounted between invar blocks; and a first electrode is connected to the first wing and a second electrode connected to the second wing communicatively coupling an electrostatic actuation device and an electrostatic detection device to the YMR, when actuated, exciting a plurality of vibrations of the cantilever of the YMR, using one or more of a plurality of excitation methods, including acoustic, photothermal and mechanical excitation methods; and a computer electro-optical device, detects reads and records measurements from a variation in a mechanical resonant frequency, to obtain a measure of stiffness of the elastic material, composing the at least one thin film deposition material, wherein a thickness of the at least one thin film deposition material ranges from a subnanometer thickness measured value to a few micrometers thickness measured value, and wherein after assessing the measure of stiffness of the elastic material, the at least one thin film deposition material ranging from the subnanometer thickness measured value to the few micrometer thickness measured value, the YMR is free of structural deformation and free of structural deconstruction.

17. The YMR according to claim 16, wherein the cantilever is a micro-cantilever having dimensions of 6.5 mm long, 1.5 mm wide and 0.3 mm thick.

18. The YMR according to claim 16, wherein the first leg and the second leg have dimensions of 0.5 mm wide, and 11.75 mm long.

19. The YMR according to claim 16, wherein the electrostatic actuation device includes an antisymmetric cantilever (ASC) device oscillating at approximately 8600 Hz.

20. The YMR according to claim 16, wherein the first and second wings vibrate 180 degrees out-of-phase, and wherein the cantilever resonator has a resolution of the achievable resonant frequency of about $2 \times 10^{-7}$, at about 10 degrees Kelvin.

* * * * *